United States Patent
Harada et al.

(10) Patent No.: US 10,264,789 B2
(45) Date of Patent: Apr. 23, 2019

(54) RODENTIA ANIMAL REPELLENT

(71) Applicant: SUMITOMO CHEMICAL COMPANY, LIMITED, Tokyo (JP)

(72) Inventors: Toshiyuki Harada, Takarazuka (JP); Chiemi Iwata, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 15/319,075

(22) PCT Filed: Jun. 16, 2015

(86) PCT No.: PCT/JP2015/067811
§ 371 (c)(1),
(2) Date: Dec. 15, 2016

(87) PCT Pub. No.: WO2015/194676
PCT Pub. Date: Dec. 23, 2015

(65) Prior Publication Data
US 2017/0118984 A1 May 4, 2017

(30) Foreign Application Priority Data
Jun. 16, 2014 (JP) .................................. 2014-123754

(51) Int. Cl.
*A01N 43/78* (2006.01)
*C07D 277/64* (2006.01)

(52) U.S. Cl.
CPC ........... *A01N 43/78* (2013.01); *C07D 277/64* (2013.01)

(58) Field of Classification Search
CPC .............................. A01N 43/78; C07D 277/64
See application file for complete search history.

(56) References Cited

U.S. PATENT DOCUMENTS

| | | | |
|---|---|---|---|
| 4,328,219 A | 5/1982 | Mues et al. | |
| 4,708,810 A * | 11/1987 | Askew ................. | C07D 277/60 252/77 |
| 4,818,535 A | 4/1989 | Baines et al. | |
| 2013/0005715 A1* | 1/2013 | Kobayakawa ......... | A01N 31/02 514/227.5 |

FOREIGN PATENT DOCUMENTS

| | | |
|---|---|---|
| CS | 120731 | 12/1966 |
| EP | 0280443 A2 | 8/1988 |
| EP | 2534949 A1 | 12/2012 |
| JP | S63-239206 A | 10/1988 |
| JP | 2002-518381 A | 6/2002 |
| JP | 2004-196684 A | 7/2004 |
| WO | WO 1999/065886 A1 | 12/1999 |
| WO | WO 2013/059364 A2 | 4/2013 |

OTHER PUBLICATIONS

Schafer et al. ("Toxicity, Repellency or Phytotoxicity of 979 Chemicals to Birds, Mammals and Plants," USDA National Wildlife Reasearch Center, Research Report No. 04-01 (2004)).*
Bouchard et al., "Chemical Analysis of Defense Secretions of *Sipyloidea sipylus* and Their Potential Use as Repellents Against Rats," *Journal of Chemical Ecology*, 23(8): 2049-2057 (1997).
Noll, "Protection of papers and paper containers against rodent attack," *Wochenblatt fuer Papierfabrikation*, 76(7): 215-218 (1948).
Schafer et al., "The Acute Oral Toxicity, Repellency, and Hazard Potential of 998 Chemicals to One or More Species of Wild and Domestic Birds," *Arch. Environ. Contam. Toxicol.*, 12(3): 355-382 (1983).
Schafer et al., "Acute Oral Toxicity and Repellency of 933 Chemicals to House and Deer Mice," *Arch. Environ. Contam. Toxicol.*, 14(1): 111-129 (1985).
Japanese Patent Office, International Search Report in International Patent Application No. PCT/JP2015/067811 (dated Sep. 15, 2015).

* cited by examiner

*Primary Examiner* — Robert H Havlin
(74) *Attorney, Agent, or Firm* — Leydig, Voit & Mayer, Ltd.

(57) ABSTRACT

Provided are a repellent having a superior repellent activity for Rodentia animal and a repellent method for Rodentia animal. A Rodentia animal repellent containing, as an active ingredient, a compound represented by the formula (1) wherein $Z^1$ is a $C_1$-$C_4$ hydrocarbon group, $Z^2$ is a hydrogen atom, or $Z^1$ and $Z^2$ are joined to form a bond, $R^1$ is a $C_1$-$C_4$ hydrocarbon group optionally having fluorine atom(s), $R^2$ is a halogen atom or a $C_1$-$C_4$ hydrocarbon group, and n is an integer of 0 to 4.

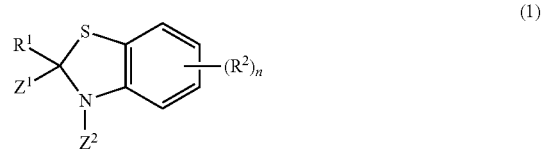

(1)

3 Claims, 1 Drawing Sheet

RODENTIA ANIMAL REPELLENT

CROSS-REFERENCE TO RELATED APPLICATIONS

This patent application is the U.S. national phase of International Patent Application No. PCT/JP2015/067811, filed on Jun. 16, 2015, which claims the benefit of Japanese Patent Application No. 2014-123754, filed Jun. 16, 2014, the disclosure of which is incorporated herein by reference in its entirety for all purposes.

TECHNICAL FIELD

The present invention relates to a rodentia animal repellent containing a (dihydro)benzothiazole compound represented by the following formula (1) as an active ingredient.

BACKGROUND ART

Conventionally, loss in life and economical loss have been caused by various problems produced by wild Rodentia animals such as damage on crops by invasion of Rodentia animals into the farmland, accidents due to invasion of Rodentia animals into road and railroad, damage by invasion of Rodentia animals into house and warehouse, biting damage on electric cable and telecommunication cable network by Rodentia animals and the like, and the like. As a countermeasure to these damages by Rodentia animals, various repellents are disclosed (patent documents 1, 2, non-patent documents 1, 2, 3).

On the other hand, a certain kind of benzothiazole compound is known to be an active ingredient of a repellent composition for insects, mite or tick (patent documents 3, 4).

To prevent the above-mentioned damages by rodentia animals, a repellent having more superior property for the animals, and a compound to be the active ingredient of a repellent are desired.

DOCUMENT LIST

Patent Documents patent document 1: JP-A-2004-196684
patent document 2: JP-A-63-239206
patent document 3: JP-A-2002-518381
patent document 4: WO 2013/59364

Non-Patent Documents non-patent document 1: Journal of Chemical Ecology (1997), 23(8), pages 2049-2057
non-patent document 2: Archives of Environmental Contamination and Toxicology (1985), 14(1), pages 111-129
non-patent document 3: Archives of Environmental Contamination and Toxicology (1983), 12(3), pages 355-382

SUMMARY OF THE INVENTION

Problems to be Solved by the Invention

An object of the present invention is to provide a repellent having a superior repellent effect for Rodentia animals, and a repellent method for Rodentia animals.

Means of Solving the Problems

Under such circumstances, the present inventors have conducted studies of various compounds and found that a compound represented by the following formula (1) has a superior repellent activity for Rodentia animal, and completed the present invention. Accordingly, the present invention is as described below.

[1] A Rodentia animal repellent comprising a compound represented by the formula (1):

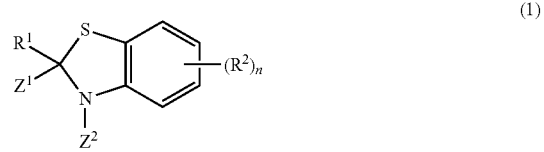

wherein $Z^1$ is a $C_1$-$C_4$ hydrocarbon group, $Z^2$ is a hydrogen atom, or $Z^1$ and $Z^2$ are joined to form a bond,
$R^1$ is a $C_1$-$C_4$ hydrocarbon group optionally having fluorine atom(s), $R^2$ is a halogen atom or a $C_1$-$C_4$ hydrocarbon group, and
n is an integer of 0 to 4
(hereinafter to be also referred to as the present compound) as an active ingredient (hereinafter to be also referred to as the repellent of the present invention).

[2] A Rodentia animal repellent comprising a compound represented by the formula (1a):

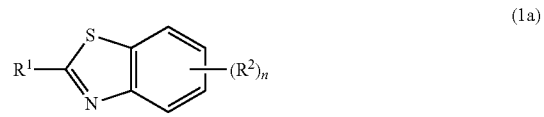

wherein $R^1$, $R^2$ and n are as defined above, as an active ingredient.

[3] A Rodentia animal repellent comprising a compound represented by the formula (1b):

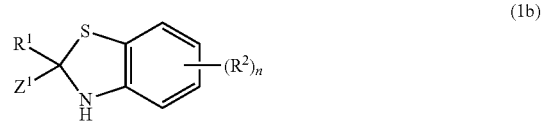

wherein $Z^1$, $R^1$, $R^2$ and n are as defined above, as an active ingredient.

[4] A method of repelling a Rodentia animal, comprising setting a compound represented by the formula (1) at a place where repelling of Rodentia animals is desired (also indicated as the method of the present invention).

Effect of the Invention

The place where the repellent of the present invention is placed can effectively repel Rodentia animals for a comparatively long period. Therefore, the damage by Rodentia animals in this place can be prevented.

DESCRIPTION OF EMBODIMENTS

Figure 1:
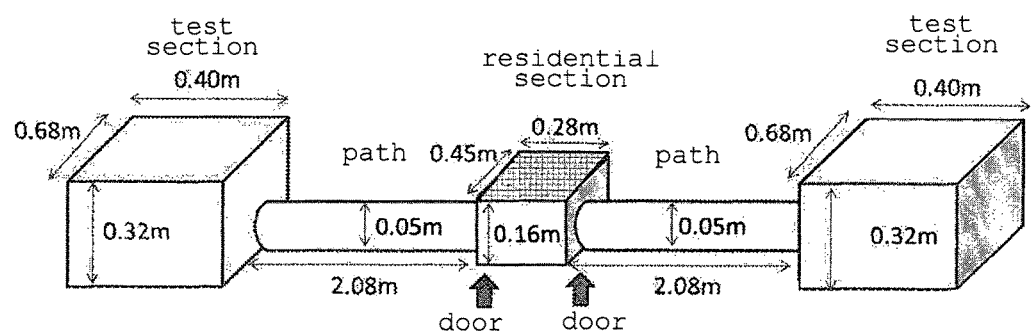
FIG. 1 is a Figure showing the general view of the repellent test apparatus used in Experimental Example 1.

The present invention is explained in detail in the following.

In the present specification, the "halogen atom" means a fluorine atom, a chlorine atom, a bromine atom or an iodine atom.

In the present specification, the "$C_1$-$C_4$ hydrocarbon group" means a $C_1$-$C_4$ alkyl group, a $C_2$-$C_4$ alkenyl group, a $C_2$-$C_4$ alkynyl group or a $C_3$-$C_4$ cycloalkyl group.

The $C_1$-$C_4$ alkyl group is a methyl group, an ethyl group, a propyl group, an isopropyl group, a butyl group, an isobutyl group, a sec-butyl group or a tert-butyl group. As the $C_2$-$C_4$ alkenyl group, a vinyl group and an allyl group can be mentioned. As the $C_2$-$C_4$ alkynyl group, an ethynyl group and a propargyl group can be mentioned. As the $C_3$-$C_4$ cycloalkyl group, a cyclopropyl group can be mentioned.

As the $C_1$-$C_4$ hydrocarbon group having fluorine atom(s), a trifluoromethyl group, a 2,2,2-trifluoroethyl group and a 2-fluoropropyl group can be mentioned.

Preferable present compounds in the present invention are as follows.
(A) A compound represented by the formula (1a)

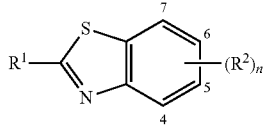

(1a)

wherein $R^1$ is a $C_1$-$C_4$ alkyl group, $R^2$ is a halogen atom or a $C_1$-$C_4$ alkyl group, and n is 0 or 1.
(B) A compound represented by the formula (1a) wherein $R^1$ is a methyl group or a trifluoromethyl group, $R^2$ is a fluorine atom or a methyl group, and n is 0 or 1.
(C) A compound represented by the formula (1a) wherein $R^1$ is a methyl group, $R^2$ is a fluorine atom or a methyl group, and n is 0 or 1.
(D) A compound represented by the formula (1a) wherein $R^1$ is a methyl group or a trifluoromethyl group, and $(R^2)_n$ is absent, a 4-methyl group or a 5-fluoro group.
(E) A compound represented by the formula (1a) wherein $R^1$ is a $C_1$-$C_4$ alkyl group, and n is 0.
(F) A compound represented by the formula (1b)

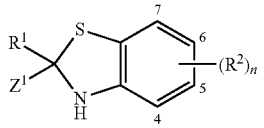

(1b)

wherein $Z^1$ is a methyl group, $R^1$ is a $C_1$-$C_4$ alkyl group, $R^2$ is a halogen atom or a $C_1$-$C_4$ alkyl group, and n is 0 or 1.
(G) A compound represented by the formula (1b) wherein $Z^1$ is a methyl group, $R_1$ is a methyl group or a trifluoromethyl group, $R^2$ is a fluorine atom or a methyl group, and n is 0 or 1.
(H) A compound represented by the formula (1b) wherein $Z^1$ is a methyl group, $R^1$ is a methyl group, $R^2$ is a fluorine atom or a methyl group, and n is 0 or 1.
(I) A compound represented by the formula (1b) wherein $Z^1$ is a methyl group, $R^1$ is a methyl group or a trifluoromethyl group, $(R^2)_n$ is absent, a 4-methyl group or a 5-fluoro group.
(J) A compound represented by the formula (1b) wherein $Z^1$ is a methyl group, $R^1$ is a $C_1$-$C_4$ alkyl group, and n is 0.

While the present compound may be a compound commercially available as a reagent and the like, or can also be produced by a known production method shown below.

Of the present compounds, a compound which is solid at ambient temperature (25° C.) can be purified by recrystallization, and a part of the compounds can be purified by distillation under reduced pressure conditions.

The present compound can be produced, for example, by the production method described in the following production method 1-production method 4.

(Production Method 1)

Of the present compounds, compound (1a) can be produced, for example, according to the following scheme.

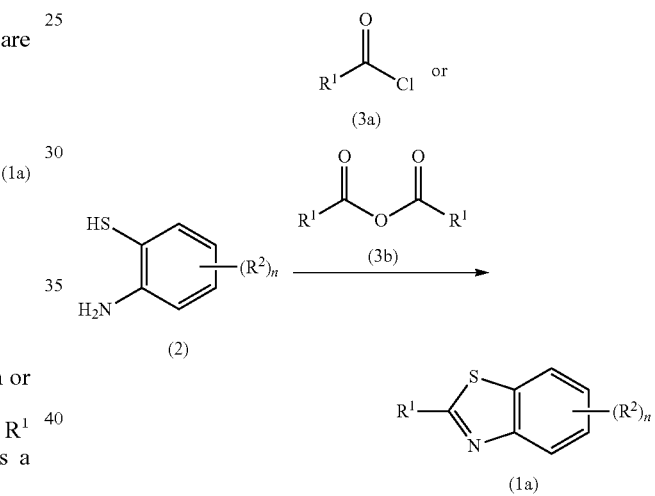

wherein $R^1$, $R^2$ and n are as defined above.

This reaction is generally performed in a solvent. Examples of the usable solvent include water; aromatic hydrocarbons such as benzene, toluene, xylene and the like; halogenated hydrocarbons such as dichloromethane, chloroform, 1,2-dichloroethane and the like; ethers such as diethyl ether, diisopropyl ether, 1,4-dioxane, tetrahydrofuran, 1,2-dimethoxyethane and the like and a mixture of these.

In this reaction, 0.1-10 mol of a base such as sodium hydroxide, triethylamine and the like is used as necessary, per 1 mol of compound (2).

The reaction temperature of this reaction is generally 0-200° C. The reaction time of this reaction is generally 5 min-several days.

The completion of this reaction can be confirmed by sampling a part of the reaction mixture and subjecting same to an analysis means such as thin layer chromatography, high performance liquid chromatography and the like. After the completion of this reaction, for example, compound (1a) can be isolated by an operation including adding water to the reaction mixture, extracting the mixture with an organic solvent, drying and concentrating the obtained organic layer, and the like. Isolated compound (1a) can also be purified by an operation such as silica gel column chromatography, recrystallization, distillation and the like.

(Production Method 2)

Of the present compounds, compound (1a) can be produced, for example, according to the following scheme.

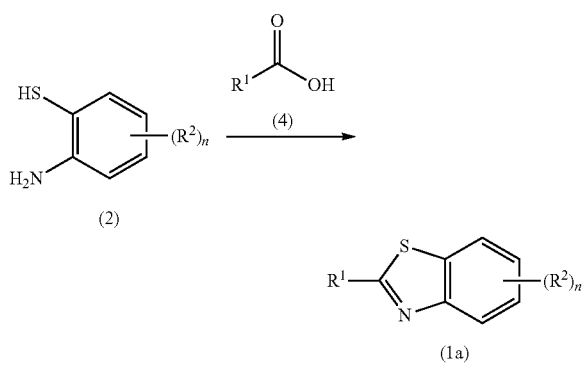

wherein $R^1$, $R^2$ and n are as defined above.

This reaction is generally performed in a solvent, or without solvent. Examples of the usable solvent include water; aromatic hydrocarbons such as benzene, toluene, xylene and the like; esters such as ethyl acetate, butyl acetate and the like and a mixture of these can be mentioned.

In this reaction, 0.1-10 mol of an acid such as methanesulfonic acid, Amberlyst (registered trade mark)-15 and the like, or a base such as phosphorus trichloride, triethylamine, N,N-diisopropylethylamine and the like is used as necessary per 1 mol of compound (2).

The reaction temperature of this reaction is generally 0-200° C. The reaction time of this reaction is generally 5 min-several days.

The completion of this reaction can be confirmed by sampling a part of the reaction mixture and subjecting same to an analysis means such as thin layer chromatography, high performance liquid chromatography and the like. After the completion of this reaction, for example, compound (1a) can be isolated by an operation including adding water to the reaction mixture, extracting the mixture with an organic solvent, drying and concentrating the obtained organic layer, and the like. Isolated compound (1a) can also be purified by an operation such as silica gel column chromatography, recrystallization, distillation and the like.

(Production Method 3)

Of the present compounds, compound (1a-1) can be produced, for example, according to the following scheme.

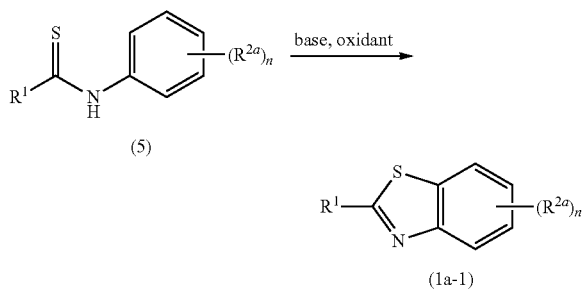

wherein $R^1$ and n are as defined above, and $R^{2a}$ is a $C_1$-$C_4$ hydrocarbon group.

This reaction is generally performed in a solvent. Examples of the usable solvent include water; alcohols such as methanol, ethanol, propanol and the like; nitriles such as acetonitrile and the like; amides such as N,N-dimethylformamide, N,N-dimethylacetamide and the like; aromatic hydrocarbons such as benzene, toluene, xylene and the like; halogenated hydrocarbons such as dichloromethane, chloroform, 1,2-dichloroethane and the like; ethers such as diethyl ether, diisopropyl ether, 1,4-dioxane, tetrahydrofuran, 1,2-dimethoxyethane and the like and a mixture of these.

Examples of the base to be used in this reaction include hydrogencarbonates such as sodium hydrogen carbonate and the like; alkali metal hydroxides such as sodium hydroxide and the like; and carbonates such as cesium carbonate and the like. In this reaction, generally 1-5 mol, preferably 1-3 mol, of a base is used per 1 mol of compound (5).

Examples of the oxidant to be used in this reaction include potassium hexacyanoferrate (III), ammonium hexanitratocerate (IV) and the like. The oxidant is generally used at 1-10 mol, preferably 1-5 mol, per 1 mol of compound (5).

The reaction temperature of this reaction is generally 0-200° C. The reaction time of this reaction is generally 5 min-several days.

The completion of this reaction can be confirmed by sampling a part of the reaction mixture and subjecting same to an analysis means such as thin layer chromatography, high performance liquid chromatography and the like. After the completion of this reaction, for example, compound (1a-1) can be isolated by an operation including adding water to the reaction mixture, extracting the mixture with an organic solvent, drying and concentrating the obtained organic layer, and the like. Isolated compound (1a-1) can also be purified by an operation such as chromatography, recrystallization, distillation and the like.

(Production Method 4)

Of the present compounds, compound (1b) can be produced, for example, according to the following scheme.

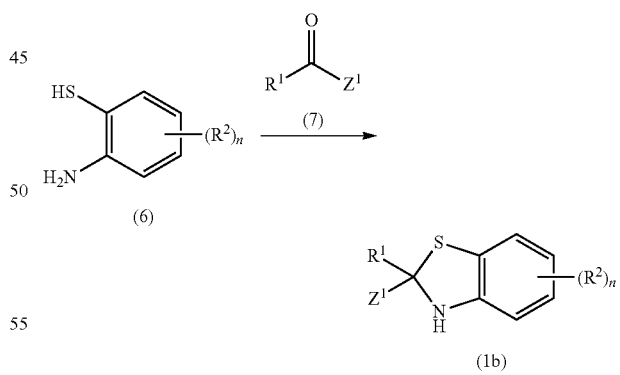

wherein $Z^1$, $R^1$, $R^2$ and n are as defined above.

While this reaction is generally performed without solvent, a solvent may also be used. Examples of the usable solvent include alcohols such as methanol, ethanol, propanol and the like; amides such as N,N-dimethylformamide, N,N-dimethylacetamide and the like; aromatic hydrocarbons such as benzene, toluene, xylene and the like; halogenated hydrocarbons such as dichloromethane, chloroform, 1,2-dichloroethane and the like, and a mixture of these.

In this reaction, generally 1-10 mol, preferably 2-5 mol, of aluminum oxide and the like is used as necessary per 1 mol of compound (6).

The reaction temperature of this reaction is generally 0-200° C. The reaction time of this reaction is generally 5 min-several days.

The completion of this reaction can be confirmed by sampling a part of the reaction mixture and subjecting same to an analysis means such as thin layer chromatography, high performance liquid chromatography and the like. After the completion of this reaction, for example, compound (1b) can be isolated by an operation including adding water to the reaction mixture, extracting the mixture with an organic solvent, drying and concentrating the obtained organic layer, and the like. Isolated compound (1b) can also be purified by an operation such as chromatography, recrystallization, distillation and the like.

(Production Method of Intermediate)

Compound (5) can be produced, for example, according to the following scheme.

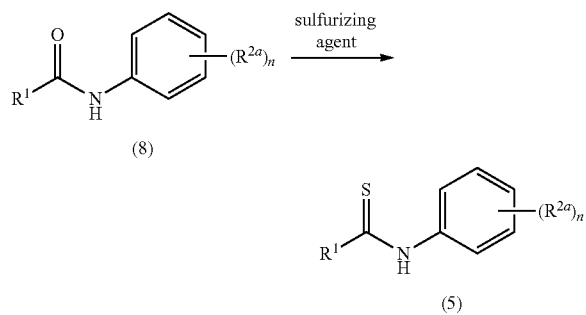

wherein $R^1$, $R^{2a}$ and n are as defined above.

This reaction is generally performed in a solvent. Examples of the usable solvent include water; nitriles such as acetonitrile and the like; aromatic hydrocarbons such as benzene, toluene, xylene and the like; ethers such as diethyl ether, diisopropyl ether, 1,4-dioxane, tetrahydrofuran, 1,2-dimethoxyethane and the like; halogenated hydrocarbons such as dichloromethane, chloroform, 1,2-dichloroethane and the like, and a mixture of these.

Examples of the sulfurizing agent to be used in this reaction include 2,4-bis(4-methoxyphenyl)-1,3,2,4-dithiadiphosphetane-2,4-disulfide (hereinafter sometimes to be indicated as Lawesson reagent), phosphorus pentasulfide, thiophosphoryl chloride and the like. In this reaction, generally 0.5-2 mol, preferably 0.5-1 mol, of a sulfurizing agent is used per 1 mol of compound (8).

The reaction temperature of this reaction is generally within the range of 0-200° C. The reaction time of this reaction is generally 5 min-several days.

The completion of this reaction can be confirmed by sampling a part of the reaction mixture and subjecting same to an analysis means such as thin layer chromatography, high performance liquid chromatography and the like. After the completion of this reaction, for example, compound (5) can be isolated by an operation including adding water to the reaction mixture, extracting the mixture with an organic solvent, drying and concentrating the obtained organic layer, and the like. Isolated compound (5) can also be purified by an operation such as chromatography, recrystallization, distillation and the like.

When the present compound is used as a Rodentia animal repellent, the present compound may be used directly, or may be formulated into liquid, powder, granule, sheet and the like, and formulated into a form known as a repellent and used. These preparations can be prepared using an additive generally used for formulation and by a known method generally used in the field of drug manufacture, pesticide, food and the like.

The repellent of the present invention is preferably formulated into a preparation capable of maintaining the efficacy of the present compound for a long term. Examples of the preparation capable of maintaining the efficacy for a long term include known sustained-release preparations and controlled-release preparations used in the fields of pesticides, foods and the like.

Examples of the additive used for the formulation of the repellent of the present invention include surfactants, solvents, inorganic carriers, polymer materials and the like.

Examples of the aforementioned surfactant include anionic surfactant, nonionic surfactant, amphoteric surfactant and cationic surfactant. Examples of the anionic surfactant include alkylbenzenesulfonate, alkanesulfonate, olefinsulfonate, monoalkylsulfuric acid ester salt, polyoxyethylene alkyl ether sulfuric acid ester salt, polyoxyethylene alkyl phenyl ether sulfuric acid ester salt and the like. Examples of these salts include alkali metal salts such as sodium salt, potassium salt and the like, alkanolamine salts such as monoethanolamine, diethanolamine, triethanolamine and the like, and the like. Examples of the nonionic surfactant include polyoxyethylene alkyl ether, polyoxyethylene alkyl phenyl ether, polyoxyethylene polyoxypropylene block copolymer and the like represented by ethylene oxide adducts of nonyl phenyl ether and higher alcohol. Examples of the amphoteric surfactant include betaine type amphoteric surfactants such as alkylbetaine, alkylamidobetaine, carbobetaine, hydroxysulfobetaine and the like, imidazoline type amphoteric surfactants and the like. Examples of the cationic surfactant include ammonium type such as alkyltrimethylammonium salt, benzalkonium type such as alkyldimethylbenzalkonium salt and the like. One or more kinds selected from these surfactants can be used.

Examples of the aforementioned solvent include solvents such as methanol, ethanol, propanol, isopropanol, ethylene glycol and propylene glycol, polymer substances thereof (polyethylene glycol and polypropylene glycol), methylcellosolve, cellosolve, butylcellosolve, propylcellosolve, diethylene glycol, methylcarbitol, carbitol, butylcarbitol, propylcarbitol, propylene glycol monomethyl ether, propylene glycol monoethyl ether, propylene glycol monobutyl ether, propylene glycol monopropyl ether, dipropylene glycol, dipropylene glycol monomethyl ether, dipropylene glycol monoethyl ether, dipropylene glycol monobutyl ether, dipropylene glycol monopropyl ether, glycerol and a derivative thereof, vegetable oil such as soybean oil, cottonseed oil and the like, petroleum aliphatic hydrocarbon and the like. One or more kinds selected from these solvents can be used.

Examples of the inorganic carrier include carriers such as mineral carriers such as kaolin clay, attapulgite clay, bentonite, montmorillonite, acid clay, pyrophyllite, talc, diatomaceous earth, calcite and the like, inorganic salts such as calcium carbonate, ammonium sulfate and the like, and the like. One or more kinds selected from these inorganic carriers can be used.

The polymer material is not particularly limited as long as the effect of the repellent of the present invention is not impaired. Examples thereof include rubber materials such as silicon rubber, acrylic rubber, guar gum, locust bean gum, natural rubber, urethane rubber, ethylene-propylene rubber (EPR), ethylene-propylene-diene rubber (EPDM), and styrene-butadiene rubber (SBR, SEBR and the like); synthetic polymers such as polyvinyl alkyl ether, polyvinyl alcohol, polyvinyl acetate, methyl vinyl ether/maleic anhydride copolymer, polyvinylpyrrolidone, carboxylvinyl polymer, vinylpyrrolidone/vinyl acetate alkylaminoacrylic acid copolymer, metacarboxybetaine/metacarboxy ester copolymer, styrene/maleic acid copolymer, ethylene/vinyl acetate copolymer, partially hydrolyzed ethylene/vinyl acetate copolymer, partially hydrolyzed polyvinyl acetate, polyethylene, polypropylene, polyethylene terephthalate, polybutylene terephthalate, polyamide, polyacetal, polyphenylene sulfide, polyimide, polyether ketone, polyether imide, polyether ether ketone, polyacrylonitrile, poly(meth)acrylic acid alkyl ester, polyalkylene oxide and the like; natural polymer materials such as chitin, chitosan, starch, collagen, pullulan, ethylcellulose, methylcellulose, acetyl cellulose, hydroxyethylcellulose, hydroxypropylcellulose, phthalate methylcellulose, carboxymethylcellulose and the like; and the like. One or more kinds selected from these polymer materials can be used.

The repellent of the present invention in a liquid form can be prepared by dissolving the present compound in the above-mentioned organic solvent, and adding the above-mentioned surfactant as necessary.

The repellent of the present invention in a powder or granular form can be prepared by mixing the present compound with the above-mentioned inorganic carrier, adding the above-mentioned surfactant as necessary, pulverizing and kneading the mixture.

The repellent of the present invention in a sheet form can be prepared by adding the present compound to a gel-like substrate of the above-mentioned polymer material, thoroughly dispersing the compound and forming same. The repellent of the present invention in a sheet form can also be prepared by supporting the repellent of the present invention in a liquid form on a fibrous sheet of the above-mentioned polymer material.

In addition, the repellent of the present invention can also be used in the form of aerosol.

The present compound can also be impregnated in or supported on a porous substance. Examples of the porous substance include zeolite, porous silica, cellulose, moist-heat treated starch, cyclodextrin, polyurethane foam, foamed polystyrene and the like. The present compound impregnated in, coated with or laminated on other substrate such as non-woven fabric, rock wool, foamed urethane, paper, cotton, felt, rope, net and the like can also be used.

The repellent of the present invention can contain additives as necessary such as other repellent, insect repellent, insecticide, bactericide, fungicide, flavor, colorant and the like.

The repellent of the present invention is effective against Rodentia animals that damage crops, forests, domestic animals, electric cables and the like, and Rodentia animals that invade into house, warehouse and the like to damage foods by eating them.

Rodentia animal is an animal also called rodent animal, and examples of the Rodentia animal include Myodonta animals such as jerboa, mole rat, rodent of Cricetidae, hamster, water vole, bank vole, black rat, brown rat, mouse, large Japanese field mouse, small Japanese field mouse, red-backed mouse, gerbil, sand rat, giant African pouched rat and the like; Castoriomorpha animals such as beaver and the like; Glirimorpha animals such as dormouse and the like; Sciurida animals such as squirrel, chipmunk and the like; and Hystricognathi animals such as spiny rat, abrocome, nutria, guinea pig and the like.

By placing the repellent of the present invention, Rodentia animals can be repelled from the place and the surrounding space where the repellent is set.

Examples of the place where the repellent of the present invention is disposed include fields, orchard, forests, breeding farm of domestic animals, road, highway, railway, airport, dust dump, park, garden, flower garden, parking lot, building, warehouse, house, kitchen, bathroom, balcony, shed, underfloor, pole, electric cable, telecommunication cable, wire mesh, fence and the like.

As a method of placing the repellent of the present invention, known methods such as simply placing the repellent of the present invention, scattering, spraying or coating same and the like can be used.

The concentration of the present compound when setting the repellent of the present invention can be appropriately determined according to the kind of the repellent target Rodentia animal, place to set the repellent, air temperature, dosage form of the repellent of the present invention and the like. The concentration of the present compound in the repellent of the present invention is, for example, 100-0.0001 wt %.

EXAMPLES

The present invention is explained in more detail in the following by referring to Examples.

First described is a production example of the present compound.

Production Example 1

To a mixture of 2-aminothiophenol (4.00 g) and toluene (26 ml) was added dropwise a mixture of propionyl chloride (2.79 ml) and toluene (14 ml) over about 10 min. Then, the mixture was stirred with heating under reflux for about 5 hr while removing water by a Dean-Stark trap. The reaction mass was cooled to room temperature, saturated aqueous sodium hydrogen carbonate solution (50 ml) was added, and the mixture was extracted twice with ethyl acetate (50 ml). The combined organic layer was washed with saturated brine (50 ml), dried over anhydrous sodium sulfate, and concentrated under reduced pressure. The residue was purified by silica gel column chromatography to give 2-ethyl-1,3-benzothiazole (hereinafter to be indicated as the present compound 2) (2.85 g).

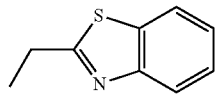

Present Compound 2:
$^1$H-NMR (CDCl$_3$) δ:7.97 (d, 1H, J=7.8 Hz), 7.85 (d, 1H, J=7.8 Hz), 7.45 (m, 1H), 7.35 (m, 1H), 3.16 (q, 2H, J=7.6 Hz), 1.48 (t, 3H, J=7.6 Hz)

Production Example 2

To a mixture of 2-aminothiophenol (4.00 g) and toluene (26 ml) was added dropwise a mixture of isobutyryl chloride (3.37 ml) and toluene (14 ml) over about 10 min. Then, the mixture was stirred with heating under reflux for about 11 hr while removing water by a Dean-Stark trap. The reaction mass was cooled to room temperature, saturated aqueous sodium hydrogen carbonate solution (50 ml) was added, and the mixture was extracted twice with ethyl acetate (50 ml). The combined organic layer was washed with saturated brine (50 ml), dried over anhydrous sodium sulfate, and concentrated under reduced pressure. The residue was purified by silica gel column chromatography to give 2-isopropyl-1,3-benzothiazole (hereinafter to be indicated as the present compound 3) (3.37 g).

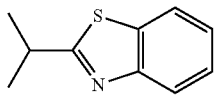

Present Compound 3:
$^1$H-NMR (CDCl$_3$) δ:7.98 (d, 1H, J=8.4 Hz), 7.85 (d, 1H, J=8.4 Hz), 7.45 (m, 1H), 7.34 (m, 1H), 3.43 (m, 1H), 1.49 (d, 6H, J=6.8 Hz)

Production Example 3

To a mixture of 2-aminothiophenol (4.00 g) and toluene (26 ml) was added dropwise a mixture of pentanoyl chloride (3.87 ml) and toluene (14 ml) over about 10 min. Then, the mixture was stirred with heating under reflux for about 10 hr while removing water by a Dean-Stark trap. The reaction mass was cooled to room temperature, saturated aqueous sodium hydrogen carbonate solution (50 ml) was added, and the mixture was extracted twice with ethyl acetate (50 ml). The combined organic layer was washed with saturated brine (50 ml), dried over anhydrous sodium sulfate, and concentrated under reduced pressure. The residue was purified by silica gel column chromatography to give 2-butyl-1,3-benzothiazole (hereinafter to be indicated as the present compound 4) (3.84 g).

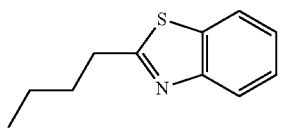

Present Compound 4:
$^1$H-NMR (CDCl$_3$) δ:7.97 (d, 1H, J=8.4 Hz), 7.84 (d, 1H, J=8.4 Hz), 7.44 (m, 1H), 7.34 (m, 1H), 3.12 (t, 2H, J=7.8 Hz), 1.87 (m, 2H), 1.48 (m, 2H), 0.98 (t, 3H, J=7.2 Hz)

Production Example 4

To a mixture of 2-aminothiophenol (3.00 g) and toluene (20 ml) was added dropwise a mixture of isovaleryl chloride (2.89 g) and toluene (10 ml) over about 10 min. Then, the mixture was stirred with heating under reflux for about 10 hr while removing water by a Dean-Stark trap. The reaction mass was cooled to room temperature, saturated aqueous sodium hydrogen carbonate solution (40 ml) was added, and the mixture was extracted twice with ethyl acetate (40 ml). The combined organic layer was washed with saturated brine (40 ml), dried over anhydrous sodium sulfate, and concentrated under reduced pressure. The residue was purified by silica gel column chromatography to give 2-isobutyl-1,3-benzothiazole (hereinafter to be indicated as the present compound 5) (3.10 g).

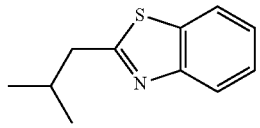

Present Compound 5:
$^1$H-NMR (CDCl$_3$) δ: 7.98 (d, 1H, J=8.0 Hz), 7.84 (d, 1H, J=8.4 Hz), 7.44 (m, 1H), 7.36 (m, 1H), 2.99 (d, 2H, J=7.2 Hz), 2.23 (m, 1H), 1.04 (d, 6H, J=6.8 Hz)

Production Example 5

A mixture of 2-aminothiophenol (4.27 ml) and trifluoroacetic acid (5.93 ml) was stirred at 70° C. for about 2 hr. The reaction mass was cooled to room temperature, and concentrated under reduced pressure. To the residue was added 1N hydrochloric acid, and the mixture was extracted with ethyl acetate. The obtained organic layer was washed with a saturated aqueous sodium hydrogen carbonate solution, dried over magnesium sulfate, and concentrated under reduced pressure. The residue was purified by silica gel column chromatography to give 2-trifluoromethyl-1,3-benzothiazole (hereinafter to be indicated as the present compound 6) (2.39 g).

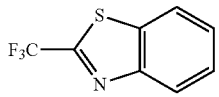

Present Compound 6:
$^1$H-NMR (CDCl$_3$) δ:8.21 (d, 1H, J=8.0 Hz), 8.01 (d, 1H, J=8.8 Hz), 7.60 (m, 2H)

Production Example 6

[Step 1]
A mixture of sodium monohydrogensulfide n hydrate (23.9 g) and ethanol (240 ml) was heated at 50° C., and thereto was added dropwise a mixture of 2-fluoro-3-nitrotoluene (13.2 g) and ethanol (100 ml) over about 1 hr. The mixture was stirred at the same temperature for about 30 min, cooled to room temperature, and concentrated under reduced pressure until the amount of the reaction mixture became about one third. Water (150 ml) was added to the residue, concentrated hydrochloric acid (30 ml) was added dropwise under ice-cooling and, after confirmation of the acidity of the liquid, the mixture was stirred for about 20 min under the same conditions. Ethyl acetate (200 ml) was added to the reaction mass, and the insoluble material was filtered and partitioned. The organic layer was washed with saturated brine (100 ml), dried over anhydrous sodium sulfate, and concentrated under reduced pressure to give a crude product containing 2-methyl-6-nitrobenzenethiol.

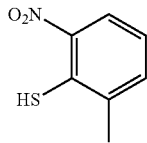

[Step 2]

To 2-methyl-6-nitrobenzenethiol crude product obtained in step 1 were added acetic acid (100 ml) and electrolytic iron powder (9.50 g), and the mixture was stirred with heating under reflux for 35 hr. The reaction mass was cooled to room temperature, methanol (100 ml) was added, the mixture was filtered through celite, and the filtered materials were washed 3 times with methanol (50 ml). The filtrate and the washing were combined, and concentrated under reduced pressure. To the residue were added silica gel (50 g) and a mixed solvent of hexane:ethyl acetate=1:1 (150 ml), and the mixture was stirred at room temperature for 30 min, filtered, and the filtered materials were washed 5 times with a mixed solvent of hexane:ethyl acetate=1:1 (100 ml). The filtrate and the washing were combined, and concentrated under reduced pressure. The residue was purified by silica gel column chromatography to give 2,7-dimethyl-1,3-benzothiazole (hereinafter to be indicated as the present compound 12) (2.67 g).

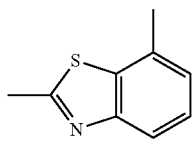

Present Compound 12:
$^1$H-NMR (CDCl$_3$) δ: 7.79 (d, 1H, J=8.0 Hz), 7.36 (m, 1H), 7.14 (d, 1H, J=7.2 Hz), 2.85 (s, 3H), 2.54 (s, 3H)

Production Example 7

[Step 1]

To a mixture of 2-acetotoluidine (5.00 g) and tetrahydrofuran (75 ml) was added a Lawesson reagent (9.48 g) and the mixture was stirred with heating under reflux for about 5 hr. The reaction mass was cooled to room temperature, water (100 ml) was added, and the mixture was extracted twice with ethyl acetate (100 ml). The combined organic layer was washed with saturated brine (100 ml), dried over anhydrous sodium sulfate and concentrated under reduced pressure. The residue was purified by silica gel column chromatography to give N-(2-methylphenyl)ethanethioamide (6.60 g).

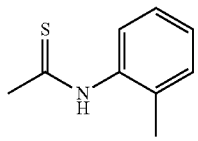

[Step 2]

To a mixture of potassium hexacyanoferrate (III) (22.1 g) and water (35 ml) was added a mixture of N-(2-methylphenyl)ethanethioamide (6.60 g) obtained in step 1, sodium hydroxide (3.69 g) and water (50 ml), and the mixture was stirred at 40° C. for about 2 hr. The reaction mass was cooled to room temperature, and the mixture was extracted twice with ethyl acetate (50 ml). The combined organic layer was washed with saturated brine (50 ml), dried over anhydrous sodium sulfate and concentrated under reduced pressure. The residue was purified by silica gel column chromatography to give 2,4-dimethyl-1,3-benzothiazole (hereinafter to be indicated as the present compound 13) (2.82 g).

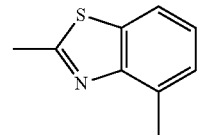

Present Compound 13:
$^1$H-NMR (CDCl$_3$) δ: 7.66 (m, 1H), 7.24 (m, 2H), 2.85 (s, 3H), 2.73 (s, 3H)

Production Example 8

A mixture of 2-aminothiophenol (4.27 ml), acetone (4.42 ml) and aluminum oxide (15 g) was stirred at room temperature for 2 hr. The reaction mass was filtered under reduced pressure, and the filtered materials were washed with chloroform. The filtrate and the washing were combined, and concentrated under reduced pressure. The residue was purified by silica gel column chromatography to give 2,2-dimethyl-2,3-dihydro-1,3-benzothiazole (hereinafter to be indicated as the present compound 14) (6.00 g).

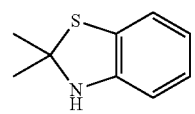

Present Compound 14:
$^1$H-NMR (CDCl$_3$) δ: 7.06 (d, 1H, J=6.8 Hz), 6.91 (t, 1H, J=6.8 Hz), 6.76 (m, 1H), 6.66 (m, 1H), 3.97 (br, 1H), 1.72 (s, 6H)

Specific examples of the present compound are shown below.

In the following Table, Me is a methyl group, Et is an ethyl group, iPr is an isopropyl group, Bu is a butyl group, and iBu is an isobutyl group.

Compound Represented by the Formula (1A)

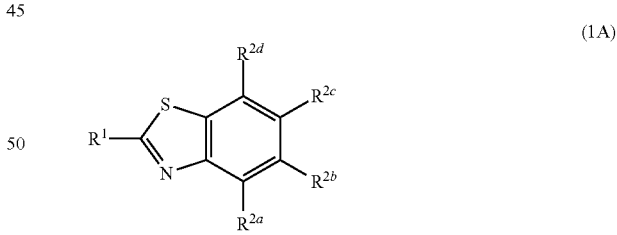

(1A)

TABLE 1

| compound No. | $R^1$ | $R^{2a}$ | $R^{2b}$ | $R^{2c}$ | $R^{2d}$ |
|---|---|---|---|---|---|
| 1 | Me | H | H | H | H |
| 2 | Et | H | H | H | H |
| 3 | iPr | H | H | H | H |
| 4 | Bu | H | H | H | H |
| 5 | iBu | H | H | H | H |
| 6 | CF$_3$ | H | H | H | H |
| 7 | Me | H | Me | Me | H |
| 8 | Me | H | Me | H | H |
| 9 | Me | H | F | H | H |

TABLE 1-continued

| compound No. | $R^1$ | $R^{2a}$ | $R^{2b}$ | $R^{2c}$ | $R^{2d}$ |
|---|---|---|---|---|---|
| 10 | Me | H | Cl | H | H |
| 11 | Me | H | H | Me | H |
| 12 | Me | H | H | H | Me |
| 13 | Me | Me | H | H | H |

Compound Represented by the Formula (1B)

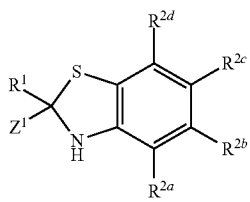

(1B)

TABLE 2

| compound No. | $R^1$ | $Z^1$ | $R^{2a}$ | $R^{2b}$ | $R^{2c}$ | $R^{2d}$ |
|---|---|---|---|---|---|---|
| 14 | Me | Me | H | H | H | H |

Now, Formulation Examples of the repellent of the present invention are described.

Formulation Example 1

Any one kind of the present compound (9 parts) is dissolved in xylene (37.5 parts) and N,N-dimethylformamide (37.5 parts), polyoxyethylene styryl phenyl ether (10 parts) and calcium dodecylbenzenesulfonate (6 parts) are added, and the mixture is stirred to give an emulsion.

Formulation Example 2

To any one kind of the present compound (20 parts) is added Sorpol 5060 (TOHO Chemical Industry Co., Ltd., registered trade mark) (5 parts), and the mixture is mixed well. CARPLEX #80 (Shionogi & Co., Ltd., registered trade mark, synthetic hydrated silicon oxide finely divided powder) (42 parts) and 300 mesh diatomaceous earth (33 parts) are added, and the mixture is mixed by a juice mixer to give a wettable powder.

Formulation Example 3

Any one kind of the present compound (3 parts), synthetic hydrated silicon oxide finely divided powder (5 parts), sodium dodecylbenzenesulfonate (5 parts), bentonite (30 parts) and clay (57 parts) are added, mixed well by stirring, an adequate amount of water is added to a mixture of these, and the mixture is further stirred, granulated by a granulator, and ventilation dried to give a granule agent.

Formulation Example 4

Any one kind of the present compound (0.5 part) is dissolved in dichloromethane (10 parts), mixed with Isopar M (isoparaffin: Exonchemical registered trade mark) (89.5 parts) to give an oil agent.

Formulation Example 5

Any one kind of the present compound (0.1 part) and Neothiosol (Chuo Kasei Co., Ltd.) (49.9 parts) are placed in an aerosol can, an aerosol valve is mounted, dimethyl ether (25 parts) and LPG (25 parts) are filled, and an actuator is mounted to give an oil aerosol.

Formulation Example 6

Any one kind of the present compound (5 parts) and soft vinyl chloride resin (95 parts) are melt kneaded by a sealed pressure kneader (manufactured by Moriyama Seisakusho), the obtained kneaded mixture is extruded by a molding machine via a molding die to give a rod formed product with length 15 cm, diameter 3 mm.

Formulation Example 7

Any one kind of the present compound (5 parts) and soft vinyl chloride resin (95 parts) are melt kneaded by a sealed pressure kneader (manufactured by Moriyama Seisakusho), the obtained kneaded mixture is extruded by a molding machine via a molding die while hot cutting to give resin pellets. The resin pellets are fed into a metal mold by an injection molding machine to give a lattice mesh formed plate.

Formulation Example 8

Any one kind of the present compound (0.5 g) is uniformly impregnated in cellulose fiber filter paper (diameter 70 mm, manufactured by Advantec Toyo Kaisha, Ltd.) to give sheet-like repellent.

Next, a superior repellent activity of the present compound against Rodentia animal is shown by way of Experimental Example. The present compounds are shown by the compound Nos. in Table 1 and Table 2, and the compound used for comparison is shown by the compound symbols of Table 3.

TABLE 3

| Compound symbol | Chemical formula | Note |
|---|---|---|
| A | (HS-benzothiazole structure) | compound described in patent document 1 |
| B | (2-phenyl-benzothiazole structure) | compound described in non-patent document 2 |
| C | (benzothiazole structure) | compound described in patent document 2, non-patent documents 1, 3 |

Experimental Example 1 (Test Animal: Mouse)

<Test Apparatus>

The repellent test was performed using the repellent test apparatus described in FIG. 1. The apparatus has a residential section for the test animal in the center part, test section 1 and test section 2 setting food on both ends, test section 1 and the residential section are connected by a cylindrical path (diameter 0.05 m, length 2.08 m), and test section 2 and the residential section are also connected by a cylindrical path. The test section 1 and test section 2 are resin cuboid shape (0.68 m×0.40 m×0.32 m) containers, and the connection parts with the paths are opened. The residential section is also a resin cuboid shape (0.28 m×0.45 m×0.16 m), and the upper part made of an iron net so that the air can be taken in. An openable door is set in the connection part between the residential section and the path. Chips for floor:clean chip SP (manufactured by CLEA Japan, Inc.) were spread all over the bottom part of the residential section.

<Acclimation Operation>

An acclimation operation was performed before the repellent test to make the test animal experienced with the test apparatus.

A weighed feed (solid food CE-2 for breeding and raising, manufactured by CLEA Japan, Inc.) (initial feed weight about 10 g) was set in each of test section 1 and test section 2, one female mouse (Jcl: ICR lineage) was placed in the residential section. One day later, the feed remaining in both test sections was weighed, and the eating rate was calculated by the following formula. When the eating rates of the both test sections are considerably different, the feed was changed to a new one, and the acclimation operation was repeated for several days until the eating rate was stabilized, and the eating rates of the both test sections became almost equivalent.

eating rate (%)=100×amount eaten (g)/initial feed weight (g)

<Repellent Test>

Figure 2:
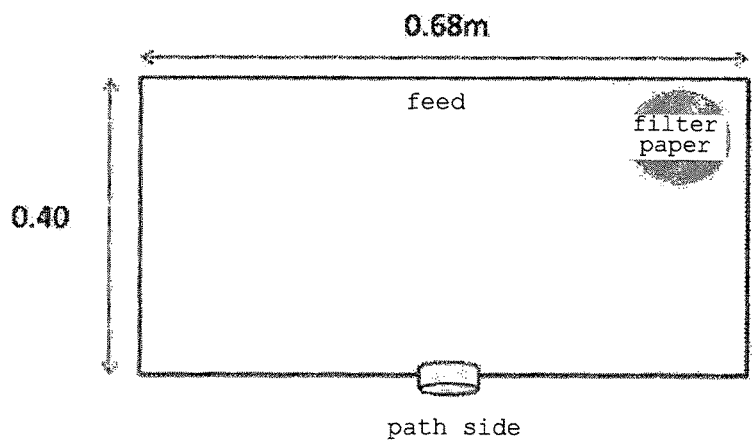
FIG. 2 is a Figure showing the arrangement of a feed and a filter paper supporting a test compound in the test section of the repellent test apparatus.

After completion of the acclimation operation, the same feed (solid food CE-2 for breeding and raising, manufactured by CLEA Japan, Inc.) (about 10 g) was placed in the both test sections. The door of the connection part between the residential section and the path was closed, filter paper supporting the test compound was set at the position described in FIG. 2 only in the test section that showed a high eating rate in the acclimation operation. After 1 hr from setting the filter paper, the door of the connection part between the residential section and the path was closed, and thereafter the door was opened. After lapse of one day from the start of the test, the feed remaining in the both test sections was weighed. When the test was continued for not less than one day, the feed in the both test sections was exchanged every other day, and the remaining feed was weighed every day.

The repellent rate was calculated by the following formula. The test section where the filter paper (diameter 70 mm, manufactured by Advantec Toyo Kaisha, Ltd.) treated with the test compound was set was taken as the treatment section, and the test section where the filter paper was not set was taken as the non-treatment section.

repellent rate (%)=100×(amount eaten in non-treatment section−amount eaten in treatment section)/(amount eaten in non-treatment section+amount eaten in treatment section)

The results of the repellent test are shown in Table 4.

TABLE 4

| Test compound | Drug amount (g) | Number of observation days (days) | repellent rate (%) |
| --- | --- | --- | --- |
| present compound 1 | 0.5 | 1 | 100 |
| | | 3 | 100 |
| | | 10 | 100 |
| | 0.1 | 1 | 100 |
| | | 3 | 100 |
| present compound 5 | 0.5 | 1 | 94 |
| present compound 6 | 0.5 | 1 | 100 |
| present compound 9 | 0.5 | 1 | 100 |
| | | 3 | 100 |
| present compound 13 | 0.5 | 1 | 100 |
| | | 3 | 100 |
| present compound 14 | 0.5 | 1 | 100 |
| | | 3 | 92 |
| comparison compound A | 0.5 | 1 | 0 |
| comparison compound B | 0.5 | 1 | 0 |
| Comparison compound C | 0.5 | 1 | 4 |

Note)
drug amount means the amount of test compound supported on one sheet of filter

INDUSTRIAL APPLICABILITY

According to the repellent of the present invention, Rodentia animal can be effectively repelled, and the damage by Rodentia animal in the place where the repellent of the present invention is set can be prevented.

This application is based on patent application No. 2014-123754 filed in Japan, the contents of which are incorporated in full herein.

The invention claimed is:

1. A method of repelling a Rodentia animal, comprising setting a compound of formula (1)

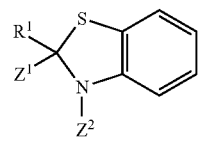

(1)

wherein
   $Z^1$ is a $C_1$-$C_4$ hydrocarbon group, $Z^2$ is a hydrogen atom, or $Z^1$ and $Z^2$ are joined to form a bond, and
   $R^1$ is a $C_1$-$C_4$ alkyl optionally having fluorine atom(s),
at a place where repelling of Rodentia animals is desired, wherein the compound of formula (1) is set apart from feed.

2. The method of claim 1, wherein the compound of formula (1) is a compound of formula (1a):

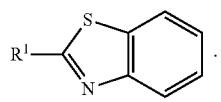
(1a)
3. A method of repelling a Rodentia animal, comprising setting a compound of formula(1b):
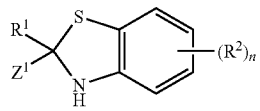
(1b)
wherein
  $Z^1$ is a $C_1$-$C_4$ hydrocarbon group,
  $R^1$ is a $C_1$-$C_4$ hydrocarbon group optionally having fluorine atom(s),
  $R^2$ is a halogen atom or a $C_1$-$C_4$ hydrocarbon group, and
  n is an integer of 0 to 4,
at a place where repelling of Rodentia animals is desired.
* * * * *